US006180671B1

(12) United States Patent
Freedman et al.

(10) Patent No.: US 6,180,671 B1
(45) Date of Patent: *Jan. 30, 2001

(54) METHODS FOR TREATING DISORDERS IN WHICH DOCOSAHEXAENOIC ACID (DHA) LEVELS ARE AFFECTED

(75) Inventors: Steven Freedman, Brighton; Juan G. Alvarez, Boston, both of MA (US)

(73) Assignee: Beth Israel Deaconess Medical Center, Inc., Boston, MA (US)

( * ) Notice: Under 35 U.S.C. 154(b), the term of this patent shall be extended for 0 days.

(21) Appl. No.: 09/248,471

(22) Filed: Feb. 11, 1999

Related U.S. Application Data (63) Continuation-in-part of application No. 09/231,479, filed on Jan. 14, 1999, now abandoned, which is a continuation-in-part of application No. 09/037,222, filed on Mar. 10, 1998, now abandoned.

(51) Int. Cl.$^7$ .................................................. A61K 31/20
(52) U.S. Cl. .......................................... 514/560; 514/558
(58) Field of Search ...................................... 514/560, 558

(56) References Cited

FOREIGN PATENT DOCUMENTS

| | | |
|---|---|---|
| 0302482 | 2/1989 | (EP) . |
| 2300807 | 11/1996 | (GB) . |
| WO 9321912 | 11/1993 | (WO) . |
| WO 9508622 | 4/1995 | (WO) . |
| WO 96/40106 | 12/1996 | (WO) . |
| WO 9836745 | 8/1998 | (WO) . |

OTHER PUBLICATIONS

Database WPI, Section Ch, Week 8035, Derwent Publications Ltd., London, GB; Class B05, AN 80–61120C, XP002108314 & JP 55 092316 A (Kagakuhin Kensa KYO), Jul. 12, 1980, Abstract.

Database WPI, Section Ch, Week 9804, Derwent Publications Ltd., London, GB; Class D13, AN 98–037227, XP002108315 & JP 09 291299 A (Nippon Oils & Fats Co. Ltd.), Nov. 11, 1997, Abstract.

Patterson, C.E. et al, "Inhibition Of Fatty Acid Synthesis Diminishes Fetal Lung Surfactant Lipid", Joint Annual Meeting of the American Lung Association and the American Thoracic Society, Kansas City, MO, May 11–14, 1986. Am. Rev. Respir. Dis. (1986) 133 (4 Suppl.), A119. CODEN: ARDSBL. ISSN: 003–0805, XP002108310 (Abstract).

Keicher, U. et al., "Omega–3 fatty acids suppress the enchanced production of 5–lipoxygenase products from polymorph neutrophil granulocytes in cystic fibrosis", Eur. J. Clin. Invest. (1995), 25(12), 915–19 CODEN: EJCIB8; ISSN: 0014–2972, 1995, XP002108311.

Baybutt, R.C. et al., "The effects of dietary fish oil on alveolar type II cell fatty acids and lung surfactant phospholipids", Lipids (Mar. 1993) 28 (3) 167–72, Journal Code: L73. ISSN: 0024–4201, XP002108312.

Mallampalli R.K. et al., "Regulation of CTP:choline–phosphate cytidylyltransferase by polyunsaturated n–3 fatty acids", Am. J. Physiol., Dec. 1994, 267 (6 PT 1) PL641–8, XP002108313.

Craig–Schmidt et al., "The Essential Fatty Acid Deficient Chicken as a Model for Cystic Fibrosis[1-4]," *American Society for Clinical Nutrition*, 44:816–24 (1986).

Gilljam, Hans et al., "Increased Mole Fraction of Arachidonic Acid in Bronchial Phospholipids in Patients with Cystic Fibrosis," *Scandinavian Journal Clin. Lab. Invest.*, 46:511–518 (1986).

Harper et al., "Essential Fatty Acid Deficiency in the Rabbit as a Model of Nutritional Impairment in Cystic Fibrosis: In vitro and in vivo Effects on Lung Defense Mechanisms[1-3]," *Am. Rev. Respir. Dis.* 126:540–547 (1994).

Hubbard et al., "Abnormal Fatty–Acid Composition of Plasma–Lipids in Cystic Fibrosis: A Primary or Secondary Defect?" *The Lancet*, (Dec. 24 and 31, 1997).

Kent et al., "Phenotypic Abnormalities in Long–Term Surviving Cystic Fibrosis Mice," *Pediatric Research*, 40:233–241 (1996).

Rivers et al., Defective Essential–Fatty–Acid Metabolism in Cystic Fibrosis, *The Lancet*, (Oct. 4, 1975).

Strandvik et al., "Relation Between Defective Regulation of Arachidonic Acid Release and Symptons in Cystic Fibrosis," *Scandinavian Journal of Gastroenterology*, 23(Suppl.):1–4 (1988).

Henderson, Jr. et al; "Oral absorption of omega–3 fatty . . . control subjects."; Journal of Pediatrics; pp. 400–409, 1994.*

* cited by examiner

Primary Examiner—Theodore J. Criares
(74) Attorney, Agent, or Firm—Lahive & Cockfield, LLP

(57) ABSTRACT

A method of treating disorders in which DHA levels are affected is described. The method includes administering to a subject suffering from the disorder a therapeutically affective amount of DHA. This method is particularly useful in treating subjects suffering from a disorder characterized by a defect in the CF, gene, e.g. cystic fibrosis, or a chronic inflammatory disorder, e.g., ulcerative colitis, Crohn's disease, chronic pancreatitis, asthma, rheumatoid arthritis or chronic gastritis. A method of ameliorating affects of cystic fibrosis in a newborn and a method of increasing surfactant levels in a fetus are also described.

27 Claims, 5 Drawing Sheets

METHODS FOR TREATING DISORDERS IN WHICH DOCOSAHEXAENOIC ACID (DHA) LEVELS ARE AFFECTED

REFERENCE TO RELATED APPLICATIONS

This application is a continuation-in-part of U.S. patent application Ser. No. 09/231,479, filed Jan. 14, 1999, entitled NOVEL, METHODS FOR TREATING DISORDERS IN WHICH DOCOSAHEXAENOIC ACID (DHA) LEVELS ARE AFFECTED, now abandoned, (which is a continuation-in-part of U.S. patent application Ser. No. 09/037,222, filed Mar. 10, 1998, entitled NOVEL METHODS FOR TREATING DISORDERS IN WHICH DECOSAHEXAENOIC ACID (DHA) LEVELS ARE AFFECTED,) now abandoned, the disclosure of which is incorporated herein by reference.

BACKGROUND OF THE INVENTION

Cystic Fibrosis (CF) is the most prevalent autosomal recessive disorder in the Caucasian population (Gorelick (1991) *Gastroenterology* 103 :681–693). Approximately 1 in 2000 live births are afflicted with CF and 5% of Caucasians in the United States are carriers of the abnormal CF gene. CF individuals rarely survive past their mid-thirties, and most mortalities are a result of recurrent pulmonary infection and, ultimately, pulmonary failure. Two other major clinical manifestations of CF are pancreatic dysfunction and male infertility.

By 1989, the CF gene had been cloned and was found to code for a chloride channel. Activation of the channel in the normal pancreas activates the chloride/bicarbonate exchanger, resulting in a net secretion of bicarbonate into the lumenal space and alkalinization of the pancreatic juice. Mutations in the chloride channel like those found in CF result in a reduced chloride conductance and a reduced ability of ductal cells to secrete bicarbonate into the lumenal space. This results in the formation of inspissated plugs within the ducts leading to obstruction of the pancreatic ducts.

In recent years, the focus in CF research has shifted towards the coupling of defective chloride channel function and membrane recycling. Recent research has demonstrated that membrane internalization at the apical plasma membrane of the pancreatic acinar cell is dependent on pH of the acinar lumen (Freedman et al., *Eur. J Cell Biol.* (1998) 75:153–63), Freedman et al., (1994) *Am. J. Physiol.* 267:G40–G51, and Freedman et al., (1994) *Eur. J. Cell Biol.* 65:354–365). Since pH of the acinar lumen is reflective of ductal bicarbonate secretion from the proximal duct cells, a phenomenon regulated via the chloride channel, a coupling may exist between duct and acinar cell function, (Freedman et al., (1994) *Am. J. Physiol.* 267:G40–G51, and Freedman et al., (1994) *Eur. J. Cell Biol.* 65:354–365). Research has also confirmed the hypothesis that lack of alkalinization of the acinar lumen leads to inhibition of apical membrane internalization and defective apical endocytosis in pancreatic acinar cells from CF mice. This block in the recycling of membranes following exocytosis leads to eventual deficiency in membranes for reformation of secretory granules. Thus, pancreatic insufficiency appears to be a result of defects in membrane recycling with obstruction of the ducts occurring as a secondary event.

Although approximately 90% of CF mortalities are the result of pulmonary infection and failure, the mechanism by which CF produces lung disease remains unknown. Abnormal and viscous mucus secretions from the pulmonary epithelia often lead to lung infections. Hydration of the secretions appears to be one underlying factor. Another factor may be the inability of CF individuals to produce dipalmitoyl phosphatidylcholine, the major component of fetal-lung surfactant, which is responsible for decreasing surface tension at the alveolar air-liquid interface. In addition, other organs, such as intestine, biliary tract and testis, become impaired due to viscous secretions. In the small intestine, this results in villous hypertrophy which compensates for decreased absorption.

Despite recent advances in our understanding of the pathogenesis of cystic fibrosis, there is no effective treatment for this life-threatening condition. As premature death is still the norm, there is a pressing need to develop novel forms of therapy to treat this disease. Although after the discovery of the gene mutation in cystic fibrosis there was great hope that gene therapy could be used as a potential treatment for this disease, these expectations were soon dismissed mainly due to (i) the inefficiency of gene transfer to epithelial cells; and (ii) the low stability over time of the transfected gene. In addition, it is not clear whether or not insertion of normal copies of the cystic fibrosis transmembrane regulator (CFTR) gene will reverse the clinical manifestations of the disease.

CF gene mutations lead to three important clinical events: 1) increased mucus secretion; 2) increased inflammatory response; and 3) decreased immune function. Previous reports have indicated that arachidonic acid (AA) levels are increased in CF patients, i.e., an increase in AA has been demonstrated in lavage fluid from the lungs of CF patients. However, this was thought to be secondary to infection and not a primary process. Our research demonstrates that there is an increase in archidonic acid (AA) while levels of docosahexaenoic acid (DHA) are significantly decreased. Thus, the ratio of DHA to AA is affected. It appears that the ratio of docosahexaenoic acid (DHA) to AA is affected. Similar findings are made in chronic inflammatory diseases.

Another condition associated with abrogated levels of DHA is respiratory distress syndrome (RDS) in premature born babies. Every year, in the United States alone, 400,000 babies are born prematurely from an estimated total of four million pregnancies. Respiratory distress syndrome due to surfactant deficiency is one of the main complications in the premature newborn. Of those babies who survive, some remain compromised with lifelong disabilities including mental retardation, cerebral palsy, deafness, and blindness.

The introduction in 1971 of the lecithin/sphingomyelin ratio in amniotic fluid as a test to predict the risk of RDS provided the obstetrician with a valuable diagnostic tool to improve the management of pregnancies at risk for premature delivery (Gluck et al., (1971) *Am. J. Obstct Gynecol.* 109:440–445). Thus, in situations where the fetal lungs are immature, the obstetrician can delay the delivery to allow the lungs to mature. However, despite the significant improvement in the accuracy of tests to predict the risk of RDS, knowledge of the maturity status of the fetal lung does not significantly change the management of these premature babies in situations where preterm deliver is imminent (e.g., preterm labor). Although corticosteriod therapy has been used to induce fetal lung maturation in pregnancies at risk for premature delivery, its use remains highly controversial and its efficacy very limited (Crowley et al., (1995) *Am. J. Obstct. Gynecol.* 173:322–335). The recent introduction of exogenous surfactant as a routine therapy to treat babies born prematurely has been a major development in efforts to decrease the severity of RDS (Cooke et al., (1995) *J. Obstct. Gynecol.* 102:679–681). However, despite the use of surfactant therapy, RDS continues to be one of the main causes of morbidity and mortality in the premature newborn. DHA treatment of the mother or newborn to prevent or treat RDS has not been used.

Thus, a need still exists to develop novel methods for treating disorders, such as cystic fibrosis and respiratory distress syndrome due to surfactant deficiency, in which DHA levels are affected.

Accordingly, an object of the invention is to provide a method for treating a disorder in which the serum, tissue or membrane levels and/or ratios of DIA and AA are affected.

Another object of the invention is to provide a method of treating cystic fibrosis in a subject by administering to the subject a therapeutically effective amount of an omega 3 fatty acid comprising 22–24 carbon atoms and 5 or more double bonds.

A still other object of the invention is to provide a method of treating a chronic inflammatory disease, e.g., ulcerative colitis, Crohn's disease, chronic pancreatitis, asthma, rheumatoid arthritis or chronic gastritis.

A further object of the invention is to provide a method for treating hypertrophy of small intestine in a subject suffering from a disorder in which DHA levels arc affected.

An additional object of the invention is to provide a method of restoring normal morphology to a cell or tissue affected with a disorder in which DHA levels are affected.

A still further object of the invention is to provide a method for diagnosing in a subject a disorder in which DHA levels are affected.

Another object of the invention is to provide a method of ameliorating affects of cystic fibrosis in a newborn.

A still additional object of the invention is to provide a method for increasing surfactant levels in a fetus.

These and other objects and features of the invention will be apparent from the following description and from the claims.

SUMMARY OF THE INVENTION

The invention features a novel method of treating a subject suffering from a disorder in which DHA levels are affected. The method includes administering to the subject a therapeutically effective amount of an omega 3 fatty acid comprising 22–24 carbon atoms and 5 or more double bonds, (e.g., DHA and DHA precursors, e.g., docosapentaenoic acid, tetracosapentaenoic acid and tetracosahexaenoic acid). The dosage may be of the fatty acid itself or in a form more easily incorporated into the tissue such as a derivative or a structured lipid. This method is particularly useful in treating subjects suffering from a disorder characterized by a defect in the CF gene, e.g., cystic fibrosis; or a chronic inflammatory disorder, e.g., ulcerative colitis, Crohn's disease, chronic pancreatitis, asthma, rheumatoid arthritis or chronic gastritis. The method is also useful in treating a disorder characterized by reduced levels of fetal surfactant, e.g., by abrogation of fetal surfactant biosynthesis.

Proper levels of treatment can be determined in a variety of ways, e.g., measurement of the DHA levels in plasma which are raised to at least about 170 $\mu$g/ml. Preferably, the DHA levels are raised to the range of about 200 $\mu$g/ml to about 500 $\mu$g/ml.

Omega 3 fatty acids comprising 22–24 carbon atoms and 5 or more double bonds may be administered in different modes, e.g., as a part of a nutritional additive or total formulation. If a total formulation is used, it can be as a part of an enteral nutrition solution, an emulsion or as a solid formulation. The therapeutically effective amount of an omega 3 fatty acid comprising 22–24 carbon atoms and 5 or more double bonds, e.g., DHA, is about 0.3–5% of the total caloric intake, preferably 0.5–3% of total caloric intake. The therapeutically effective amount of DHA should produce a pancreatic AA/DHA ratio between 0.2–1.5, a lung AA/DHA ratio between 0.1–1.6 and a blood AA/DHA ratio between 0.1–1.6. As noted, a preferred method of administration is as a structured lipid having at least one omega 3 fatty acid comprising 22–24 carbon atoms and 5 or more double bonds, most preferably with the DHA located at $R_2$ position of the structured lipid. Preferred structured lipids also include medium chain or short chain fatty acids. In some embodiments, the structured lipid has DHA (or the 22–24 carbon, 5 or more double bond omega 3 fatty acid) at two or even all three positions.

The invention also features a method of increasing the level of DHA in one or more tissues of a subject having a disorder in which DHA levels are affected. The method includes administering to the subject a therapeutic composition comprising an omega 3 fatty acid comprising 22–24 carbon atoms and 5 or more double bonds in an amount effective to raise the levels of DHA in the subject's tissue. Preferably, the therapeutic composition comprises an omega 3 fatty acid comprising 22–24 carbon atoms and 5 double bonds in the range of about 0.5–3% of the total caloric intake. Preferably, the omega 3 fatty acid comprising 22–24 carbon atoms and 5 double bonds is DHA or a structured lipid containing DHA.

Preferably, the DHA levels are increased in affected tissue, e.g., plasma, pancreatic or lung tissue, most preferably, the DMA levels are increased in plasma to at least about 170 $\mu$g/ml.

In another preferred embodiment, the disease in which DHA levels are affected is selected from the group consisting of a disorder characterized by an defect in the CF gene, e.g., cystic fibrosis, a chronic inflammatory disorder e.g., ulcerative colitis, Crohn's disease, chronic pancreatitis, asthma, rheumatoid arthritis, chronic gastritis, or lowered fetal surfactant levels.

The invention also pertains to a method of ameliorating the effects of cystic fibrosis in a newborn. The method includes administering a therapeutic composition comprising an omega 3 fatty acid comprising 22–24 carbon atoms and 5 or more double bonds to a mother during pregnancy such that the effects of cystic fibrosis in the newborn are ameliorated.

The invention further pertains to a method of increasing surfactant levels in a fetus. The method includes administering a therapeutic composition comprising an omega 3 fatty acid comprising 22–24 carbon atoms and 5 or more double bonds to a pregnant woman who may or may not be at risk for premature delivery such that the surfactant levels in the fetus are increased.

In another aspect, the invention features a method of treating hypertrophy of small intestine in a subject suffering from a disorder in which DHA levels are affected. The method includes administering to the subject a therapeutic composition comprising an omega 3 fatty acid comprising 22–24 carbon atoms and 5 or more double bonds in an amount effective to decrease hypertrophy of small intestine by at least about 25 percent.

In yet another aspect, the invention features a method of restoring normal morphology of a cell or tissue which exhibits a disease morphology associated with disorder in which DNA levels are affected. The method includes contacting a cell, e.g., a pancreatic acinar cell or a lung cell, or a tissue, e.g., in vitro or in vivo, with a therapeutically effective amount of an omega 3 fatty acid comprising 22–24 carbon atoms and 5 or more double bonds such that the normal morphology of the cell or tissue is restored.

In still another aspect, the invention also features a method of diagnosing a disorder in which DHA levels are affected. The method includes: a) obtaining a tissue biopsy from a subject; b) determining the ratio of AA to DHA in the tissue biopsy; and c) comparing the ratio in the tissue biopsy to a standard AA to DHA ratio. If the ratio in the tissue biopsy is at least about 20% higher than the standard AA to DHA ratio, this indicates that the subject is suffering from the disorder in which DHA levels are affected.

The following description and non-limiting examples further elucidate the invention.

DETAILED DESCRIPTION OF THE INVENTION

Dietary fatty acids are classified according to their chain length. Long chain fatty acids contain 14 carbons or greater and can be further characterized by the number of double bonds contained in their structure into saturated, monounsaturated and polyunsaturated subgroups. The two fatty acids essential in human nutrition are linoleic acid (18:2n-6) and α-linolenic acid (18:3n-3) from which polyunsaturated fatty acids of the omega 6 (n-6) series and omega 3 (n-3) series, respectively, are formed through enzymatic desaturation and elongation by the liver. Arachidonic acid (AA. 20:4n-6), produced from essential fatty acids of the omega 6 pathway, is a recruiter of inflammatory cells and a stimulant of mucus secretion. In contrast, docosahexaenoic acid (DHA, 22:6n-3), a fatty acid of the omega 3 pathway, increases membrane fluidity, promotes membrane fusion, and appears to directly down regulate AA levels.

It is well known that DHA and AA precursors compete for the intracellular enzymes involved in their incorporation into membrane lipids. AA has profound effects on stimulating mucus secretion, recruiting inflammatory cells, and inhibiting immune function leading to recurrent infections. DHA has multiple effects on cell membrane function. This is supported by experiments in which rabbits with essential fatty acid deficiency (resulting in DHA deficiency) demonstrate lung disease mimicking that observed in CF (Harper et al., (1994) *Am. Rev. Respir. Dis.* 126:540–547). DHA has also recently been reported to activate CTP:cholinephosphate citidyltransferase (Mallampalli et al., (1994) *Am. J. Physiol.* 267:L641–L648), a rate-limiting enzyme in the biosynthesis of fetal-lung surfactant. In addition, the feeding of rats with diets rich in DHA results in a significant increase in the production of surfactant lipids by type II alveolar cells (Baybutt et al., (1993) *Lipids* 28:167–172).

The inventors have now discovered a new lipid metabolic defect in cystic fibrosis (namely, a decrease in DHA and an increase in AA) that when corrected leads to a reversal of the clinical and histopathological manifestations of cystic fibrosis. These findings appear to explain the mucous hypersecretion, increased inflammatory response, and predisposition to recurrent infections that is observed in cystic fibrosis. Supplementation of a complete liquid enteral formulation with 35 to 40 mg/day of docosahexaenoic acid (DHA) in CF gene knockout mice (also referred to as "CFTR−/−mice") results in the reversal of the biochemical and morphologic manifestations of the disease. This therapy results in an increase in DHA levels reaching plasma levels above 170 μg/ml and a profound decrease in AA approaching levels seen in normal mice. An equivalent amount of DHA for a man with an approximately 1500–2000 Kcal/day diet (on a calorie basis) would be approximately 5–7 or more g/day. Modifications to this dosage may be used depending on effectiveness of incorporation into tissue and the form in which the dosage is given. This therapy would also find wide applicability in other disorders in which DHA levels are affected, e.g., chronic inflammatory disorders and male infertility. The invention also features a method to restoring the ratio of AA/DHA by administration of DNA precursors (See Example 8). The findings demonstrate that DHA levels are modified by administering DHA precursors (although not as effectively as administering DHA itself) which results in reversal of biochemical and morphological manifestations of the disease. For example, administration of 40 mg/day of docosapentaenoic acid (22:5n-3) to CFTR−/−mice resulted in 20% improvement in pancreatic morphology. In contrast, the administration of 40 mg/day of α-linolenic acid (18:3n-3) resulted in increased intestinal villi height, increased acinar lumen dilation and plug formation (See Example 8).

Accordingly, the invention features a method of treating a subject suffering from a disorder in which DHA levels are affected. The method includes administering to the subject a therapeutically effective amount of an omega 3 fatty acid comprising 22–24 carbon atoms and 5 or more double bonds, (e.g., DHA and DHA precursors, e.g., docosapentaenoic acid, tetracosapentaenoic acid and tetracosahexaenoic acid). In addition, derivatives of the omega fatty acids, e.g., the salt or ester form of the fatty acids, can be used. In addition, a structured lipid containing the omega 3 fatty acid can be used.

As used herein the term "treating" includes a therapeutic treatment of an existing or established disorder in which DHA levels are affected or prevention of the symptoms in a subject at risk for a disorder in which DHA levels are affected.

As used herein, the term "subject" is intended to include human and non-human animals. The term "non-human animals" includes all vertebrates, e.g. mammals and non-mammals, such as non-human primates, sheep, dog, cow, chickens, amphibians, reptiles, etc. In certain embodiments, the subject is a mammal, e.g., a primate, e.g., a human.

As used herein, the term "a disorder in which DHA levels are affected" refers to a disorder characterized by a defect in a cystic fibrosis (CF) gene, i.e., the cystic fibrosis transmembrane regulator (CFTR) gene, or a chronic inflammatory disorder. As used herein, the term "a disorder in which DHA levels are affected" does not refer to a disorder in which the primary cause of the disease is a bacterial or a viral infection. The term "chronic inflammatory disorder" refers to a disorder characterized by an infiltration of inflammatory cells, e.g., lymphocytes and/or monocytes, within a target tissue resulting in recurring or prolonged disease symptoms. The infiltration of inflammatory cells also results in increased prostaglandin synthesis which results from increased arachidonic acid (AA) levels. For example, infiltration of monocytes and lymphocytes within a target tissue results in pain and impairment of the tissue's function. Examples of chronic inflammatory disorders include, but are not limited to, ulcerative colitis, Crohn's disease, chronic pancreatitis, asthma, rheumatoid arthritis and chronic gastritis. The term "a disorder in which DHA levels are affected" is also intended to refer to a disorder associated with the regulation of surfactant levels, such as biosynthesis via activation of CDP:cholinephosphate citidyltransferase.

The term "administering" is intended to include routes of introducing to a subject DHA to perform its intended function. Administration can be carried out by any suitable route of administration. Preferred route of administration is oral administration.

As used herein, the term "therapeutically effective amount" refers to the quantity of an omega 3 fatty acid comprising 22–24 carbon atoms and 5 or more double bonds necessary to prevent, to cure or at least partially arrest the symptoms of the disorder and its complications. For example, the therapeutically effective amount of an omega 3 fatty acid comprising 22–24 carbon atoms and 5 or more double bonds is the amount sufficiently large not only to increase DHA levels in an affected cell or tissue but also to decrease AA levels in the affected cell or tissue. Preferably, the DHA levels are raised in plasma to at least about 170 $\mu$g/ml, preferably they are raised in the range of about 200 $\mu$g/ml to about 500 $\mu$g/ml, more preferably they are raised to at least about 250 $\mu$g/ml.

Amounts of an omega 3 fatty acid comprising 22–24 carbon atoms and 5 or more double bonds effective for use in the methods of the invention will, of course, depend on the severity of the disorder and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al. (eds.) (1990) Goodman and Gilman's: The Pharmacological Basis of Therapeutics, 8th ed., Pergamon Press; and Remington's Pharmaceutical Sciences, 17th ed. (1990), Mack Publishing Co., Easton, P., each of which is herein incorporated by reference. Effectiveness of the dosage can be monitored by measuring the AA to DHA ratio in affected cells or tissue, or in red blood cells as described herein. Preferably, the therapeutically effective amount of an omega 3 fatty acid with 22–24 carbon atoms and 5 double bonds, e.g. DHA, is about 0.3–5% of the total calories, more preferably it is about 0.5–3% of total caloric intake. The omega 3 fatty acid comprising 22–24 carbon atoms and 5 or more double bonds can be administered as a part of a nutritional formulation. Sources for these fatty acids include, but are not limited to, fish oils, e.g., salmon oil, and breast milk. In addition, DHA is commercially available from Martek, Inc. as a fungal derivative which contains 50% DHA. DHA-containing formulation Neuromins is commercially available from Nature's Way Products Inc., Springville, Utah. In addition, free DHA is also available from Sigma Chemical Corporation (St. Louis, Mo.) and DHA ethyl esters from Nu-Prep-Check Inc., (Elysian, Minn.). The dosage may be given either as a loading dose provided as meal feeding, or continuous parenteral or enteral administration, for the initial therapy period. This allows sufficient time for the DHA to equilibrate within the tissues (e.g. 4–6 weeks with meal feeding and about 2 days with continuous parenteral or enteral administration) which can be followed by a maintenance dose that is a small fraction of the loading dose.

An omega 3 fatty acid comprising 22–24 carbon atoms and 5 or more double bonds can also be administered in a form of an emulsion. Flavoring may also be added to the emulsion to make it more palatable for enteral use. Flavoring can be in a form of flavored extracts, volatile oils, chocolate flavoring, peanut butter flavoring, cookie crumbs, vanilla or any commercially available flavoring.

While the nutritional formulation is preferably provided in a ready-to-feed form, it may also be concentrated by increasing the percent total solids of the formula or made in powder form, both procedures being well known to those skilled in the art. The concentrate or powder are then reconstituted for feeding by adding water (tap or deionized-sterilized water).

An omega 3 fatty acid comprising 22–24 carbon atoms and 5 or more double bonds can also be administered as a part of a structured lipid. The structured lipid has a glycerol backbone with three fatty acids linked thereto. Preferably, the structured lipid has DHA located at the $R_2$ position. In certain embodiments, the structured lipid may include medium chain or short chain fatty acids, or have two or more DHA (or C22–24 omega 3 fatty acids with 5 or more double bonds) on the same backbone. The structured lipid may be manufactured by any conventional means such as transesterification but the use of blocking groups which allow positioning of the residues at specific locations is preferred. Those skilled in the art are familiar with the variety of techniques useful for directing the residues to particular locations and they need not be set forth here in detail. It appears that the use of omega 3 fatty acid moiety, e.g., DHA, in the $R_2$ position leads to a most preferred triglyceride. The preferred triglyceride improves absorption into the body as a whole and allows for ease of incorporation of DHA found at the $R_2$ position.

An omega 3 fatty acid comprising 22–24 carbon atoms and 5 or more double bonds can also be administered as a solid formulation. As used herein, the term "solid formulation" refers to an oral composition which generally includes in addition to an active compound, e.g., DHA, an inert diluent or an edible carrier. They can be enclosed in gelatin capsules or compressed into tablets. For the purpose of oral therapeutic administration, the active compound, e.g., DHA, can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The invention also pertains a method of treating hypertrophy of small intestine in a subject suffering from a disorder in which DHA levels are affected. The method includes administering to the subject a therapeutic composition comprising an omega 3 fatty acid with 22–24 carbon atoms and 5 double bonds, e.g. DHA, in an amount effective to decrease hypertrophy of small intestine. In a preferred embodiment, the treatment with DHA is effective to decrease hypertrophy of small intestine by at least about 25%, more preferably by at least about 50%, most preferably by at least about 70–75%.

As used herein, the term "hypertrophy of small intestine" refers to a condition in which there is an increase in a number of intestinal cells, e.g., columnar mucosal cells, resulting in the increase in the villi size as compared to a normal small intestine morphology. The decrease or increase in the villi size can be measured using methods described below.

The invention also pertains to a method of restoring normal morphology of a cell or tissue which exhibits a disease morphology associated with a disorder in which DHA levels are affected. The method includes contacting a cell or a tissue with a therapeutically effective amount of DHA such that the normal morphology of the cell or tissue is restored. In a preferred embodiment, the cell is a pancreatic acinar cell or a lung cell, e.g., a serous cell within the submucosal gland or a type II alveolar cell. In another preferred embodiment, the tissue is lung, pancreas or small intestine. Contacting can occur both in vitro and in vivo.

The term "disease morphology" refers to a morphology observed in an affected cell or tissue of a subject suffering from a disorder in which DMA levels are affected. Examples of disease morphology observed in affected tissues or cells include, but are not limited to, hypertrophy of the small intestine, dilatation of pancreatic ducts, appearance of mucus plugs in the pancreatic duct system, appearance of mucus plugs in the lungs, lung inflammation and decrease in apical membrane recycling of acinar cells.

The invention also features a method of diagnosing a disorder in which DHA levels are affected. The method includes: a) obtaining a tissue biopsy from a subject; b) determining the ratio of AA to DHA in the tissue biopsy; and c) comparing the ratio in the tissue biopsy to a standard AA to DHA ratio, wherein the ratio in the tissue biopsy is at least about 20% higher than the standard AA to DHA ratio, thereby indicating that the subject is suffering from the disorder in which DHA levels are affected. In a preferred embodiment, the ratio in the tissue biopsy is at least about 25%, more preferably at least about 30%, 35%, 40% or 50% higher than the standard AA to DHA ratio.

As used herein, the term "standard AA to DHA ratio" is a ratio of AA to DHA found in a subject who is not affected with a disorder in which DHA levels are affected. The standard ratio can be determined from a tissue biopsy obtained from a subject who is not affected with a disorder in which DHA levels are affected. The standard ratio can be determined using techniques known in the art, e.g., mass spectrometry, gas chromatography, infrared spectrometry or high performance thin layer chromatography (HPTLC).

The invention also pertains to a method of ameliorating effects of cystic fibrosis in a newborn. The method includes administering a therapeutic composition comprising DHA to a mother during pregnancy such that the effects of cystic fibrosis in the newborn are reduced.

The invention further pertains to a method of increasing surfactant levels in a fetus. The method includes administering a therapeutic composition comprising DHA to a pregnant woman who may or may not be at risk for premature delivery such that the surfactant levels in the fetus are increased. In addition, the method includes administering a therapeutic composition comprising DHA to all pregnant women, preferably, starting between 24 and 30 weeks gestational age until delivery. The invention also features a method of upregulating fetal lung surfactant biosynthesis during pregnancy by increasing DHA levels in the fetal lung (See Example 9). Fetal lung surfactant is produced by type II alveolar cells in the fetal lung and its consists of approximately 90% phospholipid and 10% surfactant apoprotein (Farrel et (II., (1975) Am. Rev. Resp. Dis. 111:657–688). Surfactant biosynthesis in the human fetus starts at around 30 to 32 weeks of gestational age and the concentration in lung and amniotic fluid increases linearly until term. Several mechanisms have been implicated in the initiation of fetal lung surfactant biosynthesis during pregnancy. One of the main mechanisms, is the activation of CDP:cholinephosphate citidyltransferase, a key enzyme in the biosynthesis of dipalmitoyl phosphatidycholine (DPPC), a critical component of fetal lung surfactant, comprising 90% of disaturated surfactant phosphatidylcholines (Farrel et al., (1975) Am. Rev. Resp. Dis. 111:657–688). Mallampalli et al. have recently reported that DHA, plays a critical role in the regulation of surfactant biosynthesis via activation of CDP:cholinephosphate citidyltransferase (Mallampalli et al., (1994) Am. J. Physiol. 267:641–648). The effects of DHA administration to pregnant mice on fetal lung surfactant biosynthesis is described in Example 9. The data shows that DHA readily crosses the placenta in pregnant mice and is incorporated at significant levels in fetal lung and brain (See Example 9, Tables 8 and 9). The data also demonstrates that DHA therapy increases surfactant concentration in preterm amniotic fluid to levels normally found at term (See Example 9. Table 10). DHA therapy may also be used to accelerate brain and retina maturation in preterm newborns. Intraventricular hemorrhage due to brain immaturity is one of the main causes of morbidity and mortality in newborns before 32 weeks gestational age. DHA is one of the main lipid components of brain tissue and the increase of DHA during fetal development is correlated with brain maturation. Administration of 10 or 20 mg DHA/day to preterm wild-type pregnant mice results in a significant increase in DHA in fetal brain (See Example 9, Table 9).

Mechanism of Action

The underlining mechanism(s) for the observed decrease in DHA levels is unknown. Although not wishing to be bound by theory, four different hypothesis that could explain the observed decrease in DHA levels are outlined below. They are as follows:

1) there is a partial block in DHA biosynthesis. The DHA biosynthesis pathway is outlined below.

DHA Biosynthesis
(N-3 Pathway)

2) there is a preferred esterification of AA into membrane lipids and a subsequent decrease in DHA esterification;

3) there is a decrease in DHA biosynthesis in the liver; or 4) there is a defect in the intracellular transport of DHA or DHA intermediates.

The AA pathway is an independent pathway known to compete for the same elongation and desaturation enzymes and for the site of esterification at the sn-2 position of lipids as the DHA pathway. The AA pathway is described below:

AA Biosynthesis
(N-6 Pathway)

The invention provides a method for restoring the ratio of AA/DHA by administration of DHA or its precursors or derivatives (See Example 8). DHA is known to down-regulate AA incorporation into membrane lipids and to play a major role in regulating membrane fluidity, membrane fusion, and membrane trafficking (Stillwell et al., (1997) Lipids 32:497–506; Ehringer et al., (1990) Chem. Phys. Lipids 54:79–88 and Stillwell et al., (1993) Lipids 28:103–108). Although AA levels in membrane lipids can be significantly decreased by the administration of DHA or eicosapentacnoic acid (EPA 20:5n-3), there is no known condition in which membrane-bound AA levels are increased above basal levels (Kuehl et al., (1980) Science 210:978–984). DHA and EPA are the most prominent members of the n-3 pathway. These fatty acids are the elongation and desaturation products of the essential fatty acid, α-linolenic acid (18:3n- 3). AA (20:4n-6) is the most prominent member of the n-6 pathway and is the elongation and desaturation product of the essential fatty acid, linoleic (18:2n-6). These pathways are independent from each other and are known to compete for the same elongation and desaturation enzymes and for the site of esterification at the sn-2 position of lipids.

The balance in AA and DHA content in membrane lipids varies with cell type and plays an important role in regulating cell function. Disruption of this critical balance in AA and DHA content in cell membranes could lead to the development of pathological conditions. This is best exemplified by the Zellweger syndrome, a multiorgan genetic condition that mostly affects the central nervous system characterized by a defect in polyunsaturated fatty acid biosynthesis in peroxisomes which results in a marked decrease in DHA content, neurological dysfunction, and death at an early age (Shimozawa et al., (1992) Science 255:1132–1134 and Powers el al., (1998) Brain Pathol. 8:101–120).

Although not wishing to be bound by any theory, a primary defect in DHA biosynthesis could be explained by either an impairment in the enzymes involved in the elongation and desaturation of DHA precursors or by a defect in the translocation of DHA or its intermediates between different cell compartments. Under normal conditions, α-linolenic acid from the diet or from intracellular sources is metabolized to tetracosapentanoic acid (24:6n-3) via EPA by a series of chain elongation and desaturation reactions in the endoplasmic reticulum (Katz el atl, (1996) Nutrition 12:334–339). Tetracosapentanoic acid (24:6n-3) is then translocated to the peroxisomes where it undergoes β-oxidation to produce DHA. DHA is then translocated from the peroxisomes to the endoplasmic reticulum where it is now ready to be incorporated into membrane phospholipids. Movement of 24:6n-3 and DHA between the endoplasmic reticulum, the peroxisomes, and cell membranes is mediated by specific fatty acid binding proteins. Thus, the biosynthesis of DHA requires multiple enzymatic steps and the translocation of omega 3 fatty acid intermediates between different cell compartments. CFTR, in addition to its role in regulating chloride conductance in apical membrane of epithelial cells, has been described as a multifunctional protein involved in modulation of intracellular membrane trafficking (Jilling et al., (1997) *Int. Rev Cytol* 172:193–241). Therefore, an enzymatic impairment or defect in membrane lipid trafficking could potentially lead to a decrease in membrane-bound DHA.

Based on the experiments, feeding CFTR–/–mice with DHA precursors demonstrated a partial block in DHA biosynthesis in CFTR–/–mice downstream of EPA (See Example 8). A feature of DHA biosynthesis is that the delta 6 desaturase, a key enzyme in DHA biosynthesis, is used in both the conversion of α-linolenic acid to octadecacatetraenoic acid (18:4n-3) and tetracosapentanoic acid (24:5n-3) to tetracosahexanoic acid (24:6n-3). This enzyme is also utilized in the conversion of 18:2n-6 to 18:3n-6, both AA precursors. Feeding of CFTR–/–mice with 40 mg/day of 18:3n-3 was shown to result in a decrease in both AA and DHA because 18:3n-3 may "monopolize" the delta 6 desaturase slowing the rate of conversation of 24:5n-3 to 24:6n-3 through the delta 4-independent pathway and also the conversation of 18:2n-6 to 18:3n-6 in the AA biosynthetic pathway. The results of these experiments showed that administration of 40 mg of 18:3n-3 per day to CFTR–/–mice for one week resulted in a significant decrease in phospholipid-bound AA (p<0.001) and a further decrease in phospholipid-bound DHA (p<0.001). In addition, administration of 18:3n-3 resulted in worsening of the pathological changes in the pancreas as compared to CFTR–/–controls treated with Peptamen™ (data not shown). In contrast, administration of 40 mg/day of 18:3n-3 to wild-type mice for one week resulted in an increase in phospholipid-bound DHA and a decrease in phospholipid-bound AA but did not produce any observable effects on pancreas morphology.

Eicosapentaenoic acid (EPA) (20:5n-3), a DHA precursor downstream from 18:3n-3, is known to effectively compete with AA for the site of esterification at the sn-2 position of membrane lipids. In order to ascertain whether the increase in AA observed in CFTR–/–mice is responsible for the pathological manifestations of cystic fibrosis, CFTR–/–mice were fed with 40 mg/day of EPA (20:5n-3) for one week to down-regulate membrane-bound AA levels (See Example 8). The results from these studies demonstrated that administration of EPA resulted in a significant increase in membrane-bound EPA and a significant decrease in membrane bound AA, and no significant changes in DHA levels or pancreas morphology. Although there was a slight increase in membrane-bound D1 IA, these levels were still significantly lower than those observed in wild-type mice. Administration of EPA did not produce any observable effects on pancreas morphology.

A comparison of the effects of DHA in reversing the pathological manifestation of cystic fibrosis in CFTR–/–mice by administration of n-3 fatty acids known to compete with AA and DHA biosynthesis and/or esterfication into membrane phospholipids and fish oil is shown in Example 11. Administration of oc-linolenic acid resulted in a four-fold decrease in AA, a two-fold decrease in DHA, and a significant increase in ductal dilatation in pancreas indicative of worsening of the cystic fibrosis phenotype. Administration of EPA, resulted in a four-fold decrease in AA and no significant changes in DHA levels or pancreas morphology. Similarly to EPA, administration of a dose of fish oil equivalent to 40 mg DHA, 60 mg EPA, and 15 mg LNA resulted in a three-fold decrease in AA levels and no significant changes in DHA or pancreas histopathology. Administration of docosapentaenoic acid (DPA), or DHA precursor downstream from EPA, resulted in a four-fold decrease in AA, a two fold increase in DHA, and a slight improvement in pancreas morphology. In contrast, administration of DHA at the same concentration resulted in a four-fold decrease in AA, a five-fold increase in DHA, and normalization of pancreas morphology. These results suggest that reversal of pancreatic morphology in CFTR–/–mice requires an increase in membrane bound DHA and that down-regulation of AA alone is not sufficient to correct the histopathological manifestations of cystic fibrosis in pancreas from CFTR–/–mice.

DHA therapy may also be efficacious in disorders where a membrane imbalance in AA and DHA levels may not exist; e.g., use of DHA for the treatment of adult respiratory distress syndrome (ARDS), or the use of DHA therapy to induce fetal lung maturation during pregnancy where there is no membrane lipid imbalance in AA and DHA levels in type II cells from the fetal lung.

It is also possible that normalization of pancreas and ileum histopathology by oral DHA may be due to other DHA effects unrelated to down-regulation of phospholipid-bound AA or correction of the observed membrane lipid imbalance. This is supported by the observations that (i) administration of 40 mg EPA/day to CFTR–/–mice decreased AA levels in pancreatic cells but did not have any significant effects on pancreas morphology and that (ii) administration of 40 mg DHA/day to CFTR–/–mice increased DHA levels in pancreas 3-fold above wild-type levels and corrected pancreas morphology. Since CFTR–/–mice do not express the cAMP-regulated chloride channel (Snouwert et al., (1992) *Science* 257:1083–1088), DHA therapy may be activating and/or inducing the expression of other chloride conductance pathways (e.g., calcium-activated chloride conductance) believed to compensate for the decreased CFTR-dependent chloride conductance in pancreas from CFTR–/–mice. Amelioration of the pathologic changes in cystic fibrosis by up-regulation of calcium-activated chloride conductance is supported by the observation that disease severity in pancreas from CFTR–/–mice has been reported to inversely correlate with the activity of this calcium-activated chloride channel (Gustafsson et al., (1994) *Prog. Clin. Biol. Res.* 387:21–28). Similarly, the effects of oral DHA in correcting ileal morphology may be unrelated to down-regulation of AA levels in this organ. This is supported by the observation that oral administration of DHA not only decreased ileal villous height in CFTR–/–but also in wild-type mice. DHA has been associated with the regulation of cell growth and the induction of apoptosis perhaps through the regulation of gene expression via cell cycle or early response genes. Similar processes may be operating in the ileum in response to DHA therapy (Clarke et al., (1994) *Proc. Natl. Acad Sci. USA* 91:479–483; Bruzzone et al., (1985) *Biochem. J* 226:621–624; Alvarez et al., (1995) *Mol. Reprod. Dev.* 42:334–346).

In conclusion, the results of this study indicate that administration of high doses of DHA to CFTR–/–mice corrects the membrane lipid imbalance observed in CFTR–/–mice and normalizes the histopathological manifestations of cystic fibrosis observed in the intestine and pancreas from these mice.

The invention further provides a diagnostic method of correlating plasma or red blood cell DHA or AA levels with other organs. The plasma or red blood cell levels of DHA or AA levels can be used as a diagnostic method to determine the effectiveness of treatment in the pancreas or other affected organs (See Example 10).

This invention is further illustrated by the following examples which should not be construed as limiting. The contents of all references, patent applications, patents, and published patent applications cited throughout this application are hereby incorporated by reference. The animal models used throughout the Examples are accepted animal models and the demonstration of efficacy in these animal models is predictive of efficacy in humans.

EXAMPLES

The inventors have found in CFTR-/-mice (CF knockout mice) that docosahexaenoic acid (DHA (22:6n-3)) is specifically decreased while arachadonic acid (AA (20:4n-6)), a recruiter of the inflammatory pathway, is increased compared with wild-type (WT) mice,
The following materials and methods were used:
Lipid Analysis:

Mouse pancreatic acinar and lung cell suspensions were prepared from wild type (n=3) and CFTR-/-mice (n =3) by enzymatic and mechanical dissociation. In addition, brain, kidney, heart, spleen, and blood were sonicated in 0.3M sucrose buffer. Membrane lipids were extracted from cell and organ preparations with 20 volumes of chloroform-methanol 2:1 (v/v), transmethylated with 0.5 ml of 0.1 N methanolic-NaOH/BF$_3$ reagent, and the resulting fatty acid methyl esters analyzed by gas chromatography/mass spectrometry (GC/MS). In a different set of experiments, lipids were fractionated by aminopropyl column chromatography into triglycerides, cholesterol esters, and phosphoglycerides and the fatty acid composition of each lipid class determined by a combination of enzymatic hydrolysis, transmethylation, and GC/MS.
Feeding Protocol:

Cystic fibrosis (UNC strain) and wild type mice (12–20 grams body weight) were fed with a complete liquid enteral formulation (Peptamen™, Nestle Clinical Nutrition, Inc.) supplemented with different quantities of the DHA-containing formulation Neuromins (Nature's Way Products Inc., Springville, Utah). DHA content in the Neuromins formulation was 100 mg per 500 mg of formulation. Mice were fed once a day at about 11 a.m., seven days a week with 20 ml of Peptamen™ supplemented with the various amounts of either Neuramins, free DHA (Sigma Chemical Co., Mo.) or DHA-ethyl ester (Nu-Check-Prep, Inc. Minn.) ranging from 0.5 mg/day of DHA to 40 mg/day of DHA.

Example 1

Breeding of CFTR-/-mice

A breeding colony was established using University of North Carolina (UNC) heterozygous CFTR (+/-) mice (Jackson Laboratories, Bar Harbor, Me.). Tail clip samples of 14 day-old mice were processed for analysis of genotype as previously described by Snouwaert et al. (Snouwaert et al., (1992) Science 257:1083–1088). This UNC strain of CFTR-/-mice (also referred to as "CF") is characterized by overt pancreatic and intestinal disease and mild pulmonary disease. Both wild-type and CFTR-/-were weaned at an average of 23 days of age.

Plasma levels of DHA in CF and wild-type mice were measured as described above in the method section. The results are outlined in Table 1 below.

TABLE 1

Plasma Levels of DHA in Cystic Fibrosis and Wild Type Mice

| Mice | CF-0 | CF-0.5 | CF-2 | CF-10 | CF-40 |
|---|---|---|---|---|---|
| CF | 44/38[1,2,3] | 41/40 | 99/77 | 106/133 | 230/263 |
| WT | 45/NA | NA | NA | NA | 214/194 |

[1]values are expressed in µg/mL
[2]mice were sacrificed between 9 and 10 a.m. and last fed between 3 and 4 p.m. on the day before
[3]values are for two different mice Example 2

Lung and acinar cells were isolated from a CF mouse fed with DHA formula (mouse-1, 40 mg/day DHA). The pellets (0.5 mL for pancreas cell homogenate and 0.6 mL for lung cell homogenate) were extracted with 3 mL of chloroform-methanol 2:1 (v/v). The resulting emulsion was vortexed, centrifuged at 800 g for 3 min., and the lower phase aspirated. The residual upper phase was partitioned again with 3 ml, of chloroform-methanol 2:1 (v/v), the lower phase aspirated and both lower phases combined. Fractions were evaporated to dryness, processed for fatty acid methyl esters (FAME) and were analyzed by GC-MS analysis. Aliquots of 10 µL of 17:0 methyl ester solution in hexane [1 µg/µL] were added to the samples after methylation. Total protein content in the pancreas acini homogenate was 18 mg and 9 mg in lung homogenate.
Results
Morphology Macroscopically, pancreas and intestine appeared normal after DHA treatment.
GC-MS Data

TABLE 2

Polyunsaturated fatty acid profile in CF mice fed with Peptamen ™ alone and Peptamen ™ supplemented with DHA

| | Pancreas | | | Lung | | |
|---|---|---|---|---|---|---|
| Fatty acid | WT | CF | CF-DHA | WT | CF | CF-DHA |
| 20:4n-6 | 267 | 562 | 144[1] | 136 | 230 | 75 |
| 22:4n-6 | 5 | 14 | 1.5 | 23 | 70 | 12 |
| 22:6n-3 | 73 | 23 | 167 | 89 | 40 | 167 |

[1]values are expressed in nmoles per total extract

Example 3

Lung and acinar cells were isolated from a CF and a wild-type (WT) mouse fed with DHA formula. The pellets (0.5 mL for pancreas cell homogenate and 0.6 mL for lung cell homogenate) were extracted with 3 mL of chloroform-methanol 2:1 (v/v). The resulting emulsion was vortexed, centrifuged at 800 g for 3 min., and the lower phase aspirated. The residual upper phase was partitioned again with 3 mL of chloroform-methanol 2:1 (v/v), the lower phase aspirated and both lower phases combined. Fractions were evaporated to dryness, processed for FAME and analyzed by GC-MS. Aliquots of 20 µL of 17:0 in chloroform-methanol 2:1 (v/v) were added to the samples before methylation. Total protein content in CF pancreas acini homogenate was 14 mg and 10.4 mg in lung and 30.1 and 9.9 mg, respectively.

Results
GC-MS Data

TABLE 3

Polyunsaturated fatty acid profile in CF mice fed with Peptamen ™ alone and Peptamen ™ supplemented with DHA

| | Pancreas | | | | Lung | | | |
|---|---|---|---|---|---|---|---|---|
| Fatty acid | WT | WT-D | CF | CF-D | WT | WT-D | CF | CF-D |
| 20:4n-6 | 267 | 82 | 562 | 67[1] | 136 | 28 | 230 | 60 |
| 22:4n-6 | 5 | 1.6 | 14 | 0.4 | 23 | 2 | 70 | 4.1 |
| 22:6n-3 | 73 | 200 | 23 | 148 | 89 | 227 | 40 | 222 |

[1]values are expressed in nmoles per total extract
D: docosahexaenoic acid

TABLE 4

Summary Table of DHA supplementation data

| Organ | CF-DHA* | CF-DHA** | WT | CF |
|---|---|---|---|---|
| Pancreas | | | | |
| 20:4n-6 | 144[1] | 67 | 267 | 562 |
| 22:4n-6 | 1.5 | 0.4 | 5 | 14 |
| 22:6n-3 | 167 | 148 | 73 | 23 |
| Lung | | | | |
| 20:4n-6 | 75 | 60 | 136 | 230 |
| 22:4n-6 | 12 | 4.1 | 23 | 70 |
| 22:6n-3 | 167 | 222 | 40 | 89 |

[1]values are expressed in nmoles per total extract
(*)mouse-1 was started on DHA formulation (40 mg/day DHA) on day 30 and sacrificed on day 37
(**)mouse-2 was started on DHA formulation (40 mg/day DHA) on day 24 and sacrificed on day 47.

Example 4

Lung and acinar cells were isolated from CF mice fed with different doses of DHA, i.e., 0.5 mg/day, 2.0 mg/day, 10 mg/day or 40 mg/day DHA. The pellets were extracted with 3 mL of chloroform-methanol 2:1 (v/v). The resulting emulsion was vortexed, centrifuged at 800 g for 3 min., and the lower phase aspirated. The residual upper phase was partitioned again with 3 mL of chloroform-methanol 2:1 (v/v), the lower phase aspirated and both lower phases combined. Fractions were evaporated to dryness, processed for FAME and analyzed by GC-MS. Aliquots of 30 $\mu$L of 17:0 in chloroform-methanol 2:1 (v/v) were added to the samples before methylation.

TABLE 5

Polyunsaturated fatty acid profile in pancreas from CF mice fed with different doses of DHA

| Fatty acid | CF | CF-0.5 | CF-2 | CF-10 | CF-40 |
|---|---|---|---|---|---|
| 20:4n-6 | 267[1,2] | 315 | 233 | 177 | 67 |
| 22:4n-6 | 14[2] | 8.3 | 7.2 | 3.7 | 0.4 |
| 22:6n-3 | 23[2] | 39 | 43 | 67 | 148 |

[1]values represent the mean of three experiments
[2]values are expressed in nmoles per total extract Example 5

Figure 1:
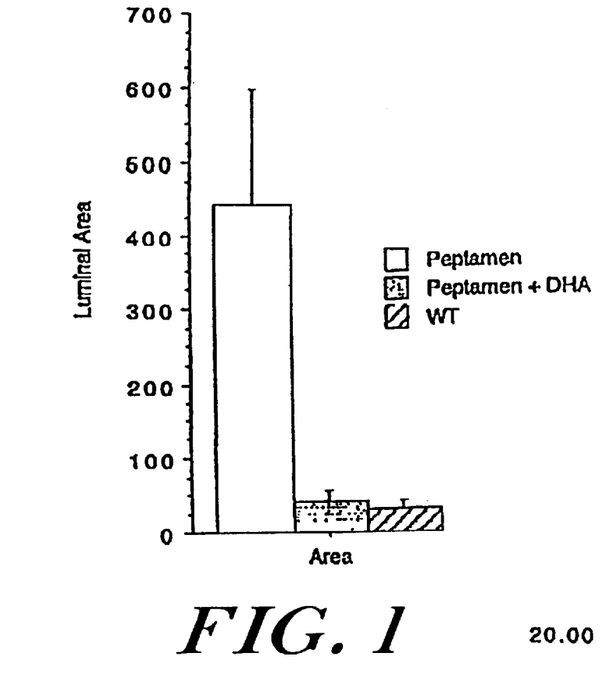
FIG. 1 is a bar graph depicting effects of DHA therapy on pancreatic luminal diameter in CFTR−/−mice (CF) and wild-type (WT) mice.

CF and WT mice were fed as outlined in the method section above. Dilation of the pancreatic duct lumen is a hallmark feature of cystic fibrosis. Therefore, the luminal area was measured from a minimum of 30 images from CF knockout mice treated with Peptamen™ alone or Peptamen™ plus 40 mg/day of DHA as well as wild type (WT) mice treated with Peptamen™ alone beginning at the time of weaning. Animals were sacrificed at 37 days of age and each pancreas fixed in glutaraldehyde. Analysis was performed using NIH Image software. The results are outlined in FIG. 1. Compared with wild-type mice, the luminal dilatation is significantly increased in CF mice. Following DHA treatment of CF mice, the ductal dilatation decreases significantly (p=0.014) to values approaching those observed in wild-type mice. No other treatment to date has shown tissue improvements at a morphological level. Furthermore, the data indicate that only higher doses of DHA, e.g., 35 to 40 mg/day of DHA, produce morphological changes in CF mice. The lower doses of DNA which have been previously reported to increase DNA plasma levels (such as described in WO96/40106) do not result in the morphological changes observed in the experiments outlined above.

Example 6

Figure 2:
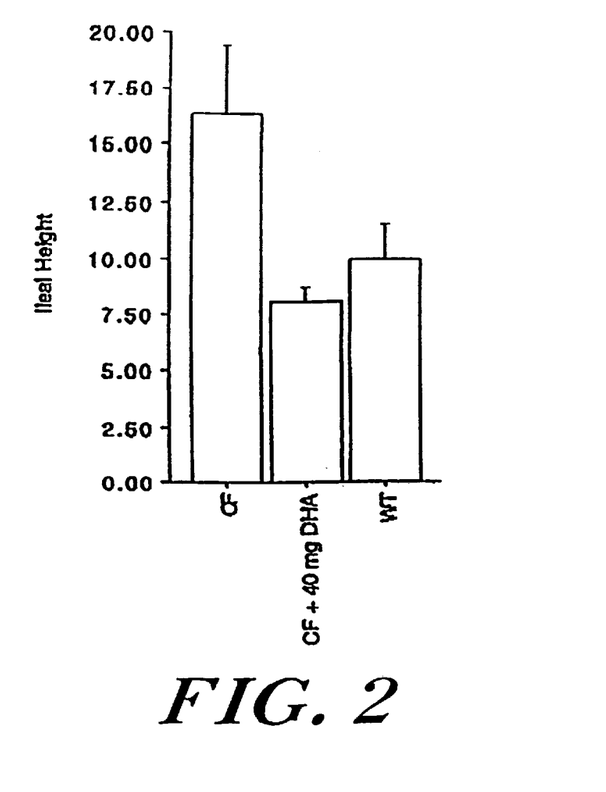
FIG. 2 is a bar graph depicting effects of DHA therapy on ileal height in CFTR−/−mice (CF) and wild-type (WT) mice.

CF and WTF mice were fed as outlined in the method section above. Ileal height, i.e., the villi height in the ileum, was measured in CF knockout animals treated with either Peptamen™ alone, Peptamen™+40 mg per day DHA, or Wild Type (WT) animals treated with Peptamen™ alone. Animals were sacrificed at 50 days of age, ileum fixed in paraformaldehyde, and the height measured on micrographs at 100×. Villi height in the ileum was found to be significantly greater compared to wild-type mice. The results are outlined in FIG. 2. Treatment of these CF mice with 40 mg DHA/day resulted in a decrease in villi height to values observed in wild-type animals. Statistically significant differences (p<0.005) were found between wild-type and CF mice as well as between CF+40 mg DHA/day and CF. There was no statistically significant difference between WT and CF+40 mg DHA/day. Significant morphological improvements in the ileal were observed in CF mice. No other treatment to date has shown tissue improvements at a morphological level. Furthermore, the data indicate that only higher doses of DHA, e.g., 35 to 40 mg/day of DHA, produce morphological changes in CF mice. The lower doses of DHA which have been previously reported to be useful in treatment of neurological disorders (such as described in WO96/40106) do not result in the morphological changes observed in the experiments outlined above.

Example 7

This example was designed to show the parallel between DHA and AA levels and the morphological effects on various tissue using DHA.

A. Cell and tissue preparation

CFTR−/−mice were prepared as described in Example 1. Both CFTR−/−mice and wild type mice were euthanized with carbon dioxide, and cell suspensions from pancreas and lung isolated. Pancreatic acini were prepared by collagenase and mechanical dissociation (Bruzzone et al., (1985) *Biochem. J* 226:621–624). A total lung cell suspension was prepared by first flushing contaminating blood by repeated injection of lung with Krebs Henseleit buffer (KHB). Tissue was then extensively minced and incubated for 30 minutes at 37° C. in 10 ml of KHB containing 1,000 units of collagenase (Worthington Biochemical, PA) 2,000 units of DNase, and 0.5 units of thermolysin (Sigma Chemical Co., St. Louis, Mo.). The resulting cell suspension was sedimented once through KHB containing 5% BSA and subsequently washed once in KHB, pH 7.4 containing 32 mM bicarbonate, 10 mM Hepes, and 0.5% BSA. Brain, kidney, and heart were removed and sonicated in 0.5 ml. and 0.3M sucrose. A similar approach was used for duodenum and ileum except that mucosal scrapings were used for sonication.

B. Analysis of AA and DHA by gas chromatography/mass spectrometry (GC/MS)

Since the pancreas and the lung are the two primary organs affected in cystic fibrosis, AA and DHA levels in cell preparations of these organs and in wild-type and CFTR−/− mice were quantitated by GC/MS analysis. Lipids were extracted from cell suspensions, tissue homogenates, and blood plasma with 6 volumes of chloroform-methanol (2:1, v/v). The resulting emulsions were centrifuged at 600 g for 3 min and the lower phase containing the lipids was collected. This procedure was repeated twice and the lower phases from the two extractions combined. Aliquots of 30 μL of heptadecanoic acid (17:0) (1 mg/ml) were added to the extracts and used as an internal standard. Samples were evaporated to dryness under nitrogen. The resulting lipids were subsequently transmethylated using the 0.1N methanolic NaOH/boron trifluoride reagent (Alvarez el al., (1995) *Mol. Reprod. Dev.* 42:334–346). The resulting fatty acid methyl esters were analyzed by Hewlett Packard GC/MS mounted with a WCOT capillary column (Supelcowax-10, 30 m×0.53 mm I.D., 1 μm film thickness) with initial and final temperatures in the column oven of 150° C. and 250° C., respectively, programmed to increase at a rate of 10° C./min. Fatty acid methyl ester peaks were identified by comparison of retention times of standard fatty acid mixtures and by mass spectrometry, and quantified using methylheptadecanoate as the internal standard. In some studies, the different lipid classes including cholesterol esters, triglycerides, free fatty acids, and glycerolipids, were also fractionated from cell and tissue extracts by aminopropyl column chromatography and the corresponding fatty acid methyl esters prepared and analyzed (Alvarez et al., (1992) *J. Chromatogr. B.* 577:142–145). In order to determine the fatty acids bound to the sn-2 position of lipids, the phospholipid fraction obtained by aminopropyl column chromatography was incubated at 37° C. for 15 min in 0.5 ml of PBS containing 250 units of phospholipase $A_2$, and the resulting fatty acids methylated and analyzed by GC/MS (Alvarez et al., (1995) *Mol. Reprod. Dev.* 42:334–346).

C. Analysis of AA and DHA by high-performance thin-layer chromatography

Aliquots of 4 μl of the fatty acid methyl esters were applied to Whatman HP-K silica gel plates, predeveloped in chloroform-methanol (1:1, v/v), and developed in hexane-ether (95:5, v/v). Following development, the plates were thoroughly dried, dipped for 5 sec in a 10% solution of $CuSO_4$ in 8% $H_3PO_4$, and placed on a CAMAG TLC plate heater III at 185° C. for 5 min. (Alvarez el al, (1995) *J. Chromatogr. B.* 665:79–87). The resulting bands were scanned at 400 nm in the reflectance mode using a CS-9000 spectrodensitometer.

D. Morphological studies

The morphology of various organs were also studied. Sample preparation were carried out as follows: 1–2 cm of ileum adjacent to the cecum was fixed in formalin, embedded in paraffin, cut in cross-section, and stained with hematoxylin/eosin. For pancreatic analyses, 2–3 mm pieces of pancreas were fixed for 1.5 h in 2% glutaraldehyde in 0.2M cacodylate buffer. Tissue samples were then washed in 0.2M cacodylate buffer and subsequently postfixed for 1 h in 1% osmium tetroxide in 0.1M cacodylate buffer. Tissue was embedded in epon and thick sections stained with 1% toluidine blue.

Morphometry: For measurement of ileal villus height or pancreatic luminal diameter, multiple images were randomly taken at 200× using a Nikon Microphot-SA microscope equipped with a Diagnostic Instruments, Inc., Spot Digitizing System. Images were examined in a blinded fashion by two independent observers. Quantitation was performed using NIH Imaging Software. The differences between the means in the groups tested were evaluated using the Student's t-test.

E. Results.

Figure 3A:
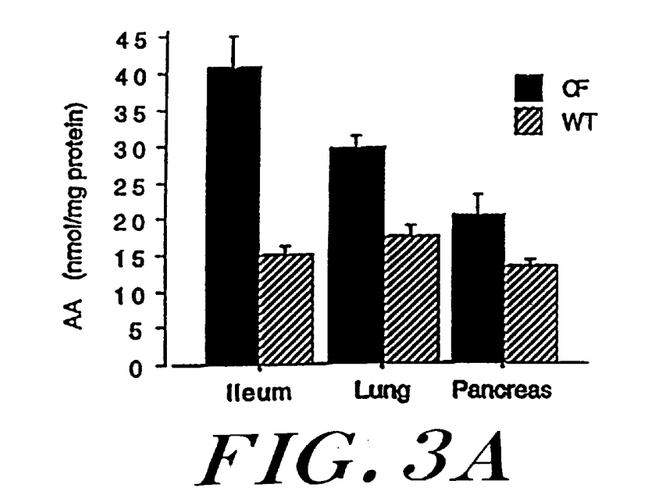
FIGS. 3a and 3b are bar graphs depicting AA and DHA levels, respectively, in various organs in CFTR (−/−) mice (CF) and wild type mice (WT).
Figure 3B:
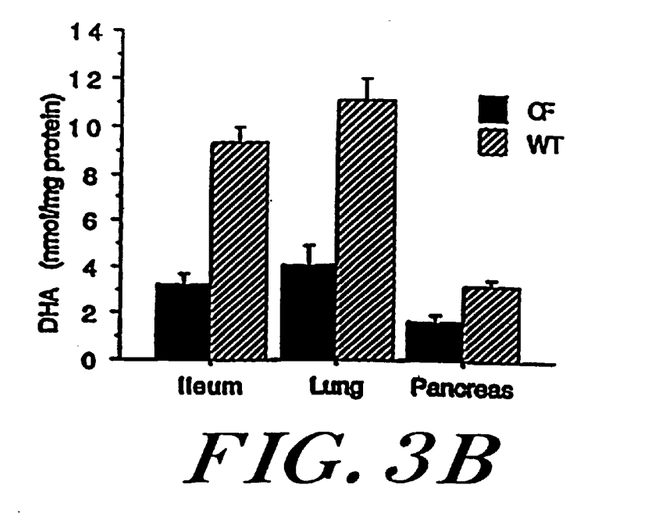

1. Phospholipid-bound AA is increased and phospholipid-bound DHA is decreased in pancreas, lung, and ileum from CFTR−/−mice AA and DHA levels in cell preparations of these organs from wild-type and CFTR−/−mice were quantitated by GC/MS analysis (See FIG. 3). AA and DHA levels were quantitated in the lung and pancreas and expressed as nmol/mg protein, results are expressed as the mean ±S.D. (n=7). In a total lung cell preparation, AA levels were approximately two-fold higher while DHA levels were two-fold lower in CFTR−/−mice compared with wild-type controls ($p<0.0001$). Similarly, in pancreatic acini preparations, there was a significant increase in AA ($p<0.01$) and marked decrease in DHA ($p<0.0001$) in CFTR−/−mice compared to wild-type controls. Greater than 95% of the AA and DHA analyzed were esterified to the sn-2 position of phospholipids as determined by aminopropyl column chromatography, enzymatic hydrolysis $A_2$, and GC/MS.

Figure 4A:
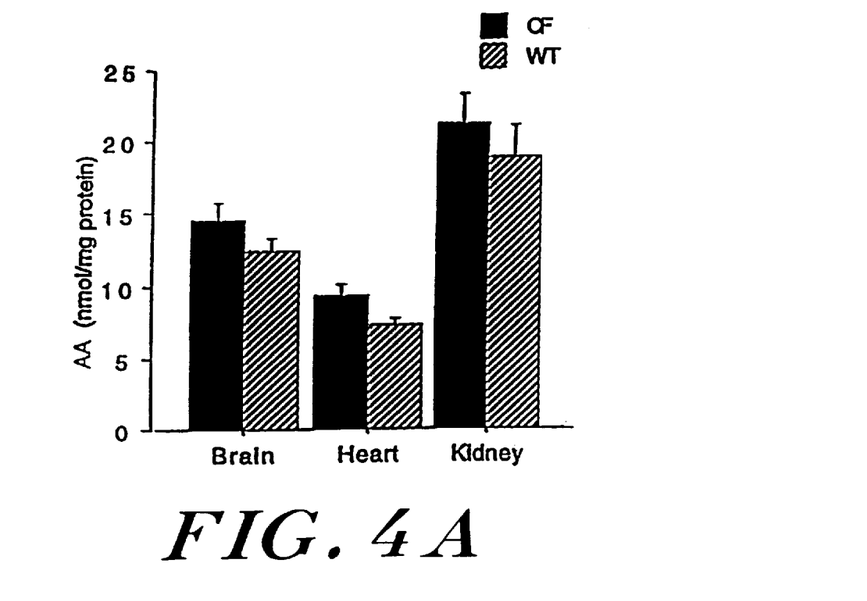
FIGS. 4a and 4b are bar graphs depicting AA and DHA levels, respectively, in other organs from CFTR (−/−) mice (CF) and wild type mice (WT).
Figure 4B:
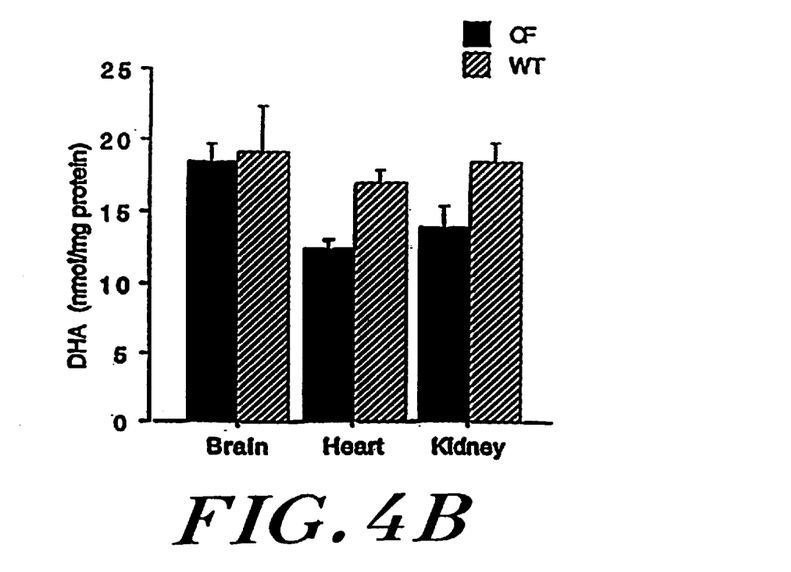

Other tissues were analyzed to determine if the lipid imbalance observed in pancreas and lung of CFTR−/−mice was specific to organs clinically affected in cystic fibrosis. Total homogenates of brain, kidney, and heart (organs not clinically affected in cystic fibrosis) showed no statistically significant changes in AA and DHA levels in CFTR−/− compared to wild-type mice (See FIG. 4). The results in FIG. 4 are expressed as the mean ±S.D. (n=3). The asterisks indicates $p<0.005$. Note, however, that these organs from CFTR−/−mice demonstrated a trend toward increased levels of AA and decreased levels of DHA compared to wild-type controls, most notably in the heart. This may be explained by the fact that CFTR (−/−)-containing cells are present to some degree in all organs, with heart containing a significant number of cells regulated by CFTR−/−dependent chloride conductance (James et al., (1996) *Circ, Res.* 79:201–207).

In contrast, mucosal scrapings of ileum from CFTR−/− mice, an organ significantly affected in cystic fibrosis, demonstrated a marked increase in AA and a significant decrease in DHA compared to wild-type mice, similar to the findings observed in pancreas and lung (See FIG. 4). This suggests that the phenotypic expression of cystic fibrosis may be related to this alteration in membrane lipids. This link between CFTR and the observed membrane lipid imbalance is further supported by the fact that the pancreatic acini preparation contains acinar, centroacinar, and proximal intralobular duct cells, all of which are known to express CFTR, based on immunohistochimicical localization studies (Marino el al., (1991) *J. Clin. Invest.* 88:712–716 and Zeng el al., (1997) *Am. J. Physiol.* 273:C442–455).

With the exception of the increase in phospholipid-bound docosatetraenoic acid (22:4n-6) observed in pancreas and lung from CFTR−/−mice, no other reproducible lipid changes were found in CFTR−/−mice compared to wild-type controls.

2. Alterations in AA and DHA levels with oral administration of DHA To observe the effect of different doses of DHA on AA and DHA levels, DHA was orally administered to CFTR−/−mice for 7 days at different concentrations. AA and DHA levels were analyzed in pancreatic and lung cell preparations by GC/MS. Since CFTR-/-mice need to be maintained on a liquid diet in order to prevent intestinal obstructions, wild-type and CFTR-/-mice were fed with either Peptamen™ (Nestle Clinical Nutrition, Inc.) (a complete liquid enteral formulation comprised of medium-chain triglycerides, carbohydrates, and hydrolyzed protein) or Peptamen™ supplemented with DHA as a stable emulsion (Kent et al., (1996) Ped. Res. 40:233–241). The results are expressed as the mean nmoles of lipid/mg protein ±S.D. as a function of mg of DHIA administered orally per day (n=3) and are shown in Table 6 below.

TABLE 6

Alterations in AA and DHA levels with oral administration of DHA.

| DHA (mg/day) | | AA/DHA Ratio |
|---|---|---|
| Pancreas | | |
| 0 | WT (Peptamen ™ alone) | 3.27 – 6.73 (4.37 ± 1.1) |
| 40 | WT (Peptamen ™ + 40 mg/day DHA) | 0.41 – 1.00 (0.62 ± 0.27) |
| 0 | CFTR-/-(Peptamen ™ alone) | 3.52 – 24.9 (13 ± 7.8) |
| 0.5 | CFTR-/-(Peptamen ™ + 0.5 mg/day DHA) | 3.93 – 7.97 (5.86 ± 2.0) |
| 2.0 | CFTR-/-(Peptamen ™ + 2.0 mg/day DHA) | 2.84 – 5.50 (4.16 ± 1.3) |
| 10 | CFTR-/-(Peptamen ™ + 10 mg/day DHA) | 1.91 – 2.13 (2.23 ± 0.38) |
| 40 | CFTR-/-(Peptamen ™ + 40 mg/day DHA) | 0.45 – 1.37 (0.87 ± 0.26) |
| Lung | | |
| 0 | WT (Peptamen ™ alone) | 1.22 – 2.0 (1.75 ± 0.47) |
| 40 | WT (Peptamen ™ + 40 mg/day DHA) | 0.20 – 0.55 (0.31 ± 0.16) |
| 0 | CFTR-/-(Peptamen ™ alone) | 2.06 – 17.8 (9.05 ± 6.8) |
| 0.5 | CFTR-/-(Peptamen ™ + 0.5 mg/day DHA) | 1.63– 2.67 (2.17 ± 0.52) |
| 2.0 | CFTR-/-(Peptamen ™ + 2.0 mg/day DHA) | 1.48– 2.31 (1.86 ± 0.42) |
| 10 | CFTR-/-(Peptamen ™ + 10 mg/day DHA) | 0.87– 1.10 (0.94 ± 0.13) |
| 40 | CFTR-/-(Peptamen ™ + 40 mg/day DHA) | 0.26– 1.44 (0.50 ± 0.3) |

Figure 5A:
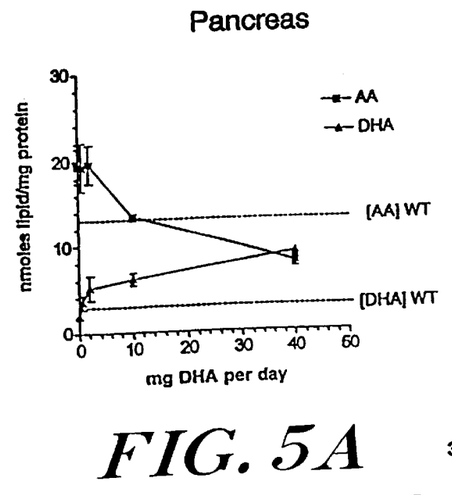
FIGS. 5a and 5b are graphs showing the effects of oral DHA administration at various concentrations on AA and DHA levels in preparations of pancreatic acini and lung cells from CFTR (−/−) mice (CF) as compared with wild-type mice (WT).
Figure 5B:
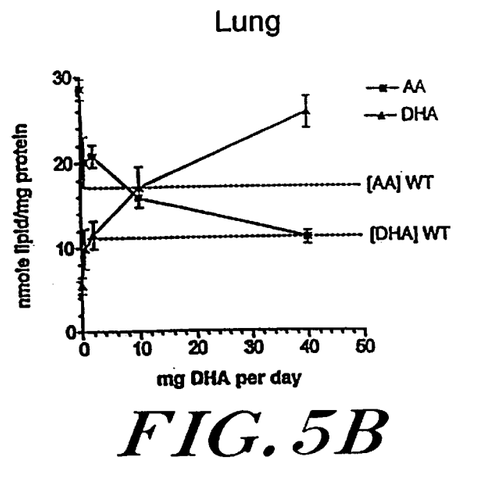

FIG. 5 shows the effects of oral DHA administration on AA and DHA levels in preparations of pancreatic acini (FIG. 5a) and lung cells (FIG. 5b). The results are expressed as the mean nmoles of lipid/mg protein ±S.D. as a function of mg of DHA administered orally per day (n=3). For reference, mean AA and DHA levels from wild type mice (WT) are indicated by the dashed lines. The results show that administration of DHA 0.5 and 2 mg per day for 7 days did not significantly alter AA levels in pancreatic acini preparations from CFTR-/-compared to wild-type mice (See FIG. 5b). Administration of DHA 10 mg per day resulted in a significant decrease in AA levels in CFTR-/-mice below those seen in wild-type mice with further suppression as DHA was increased to 40 mg per day. At 0 and 0.5 mg of DHA per day, the DHA levels in CFTR-/-mice were similar to those seen in wild-type mice, but administration of 2, 10 and 40 mg of DHA per day increased DHA levels to values higher than those observed in wild-type mice.

Similar results were obtained for AA and DHA content in lung cell suspensions following administration of varying doses of DHA (See FIG. 5a). Oral doses of 20 mg of DHA per day and higher resulted in a significant decrease in AA levels below those seen in wild-type mice. Similarly, a significant increase in DHA levels above wild-type values was only observed in mice fed DHA at doses of 2 mg per day or higher. Thus, oral administration of ≧10 mg of DHA per day for 7 days to CFTR-/-mice resulted in a decrease in AA levels below those observed in wild-type mice while significantly increasing DHA levels in pancreas and lung. However, as earlier described, only higher doses showed significant morphological changes.

Figure 6:
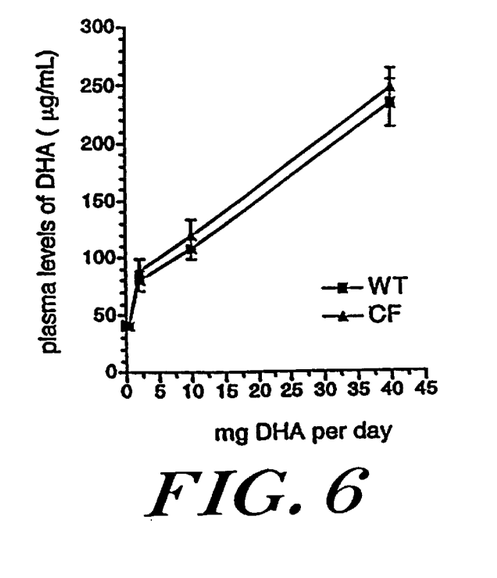
FIG. 6 is a graph depicting DHA plasma levels in wild-type (WT) and CFTR (−/−) mice as a function of oral DHA dosing.

3. The decrease in DHA levels is not due to defects in intestinal absorption or hepatic biosynthesis Endogenous plasma levels of DHA in CFTR-/-and wild-type mice fed with Peptamen were not significantly different (p=0.6), indicating that DHA biosynthesis in the liver is not affected in CFTR-/-mice (Scott el al., (1989) Proc. Natl. Acad. Sci USA 86:2903–2907). As shown in FIG. 6, DHA plasma levels in CFTR-/-and wild-type mice following administration of increasing doses of DHA were not significantly different (p=0.5) indicating that the intestinal absorption of DHA was not affected in CFTR-/-mice. The results in FIG. 6, are expressed as mean plasma level ±S.D. (n=3). No overt diarrhea was observed in CFTR-/- or wild-type mice following administration of 40 mg per day of DHA.

4. Oral administration of DHA reverses pancreatic pathology

Figure 7:
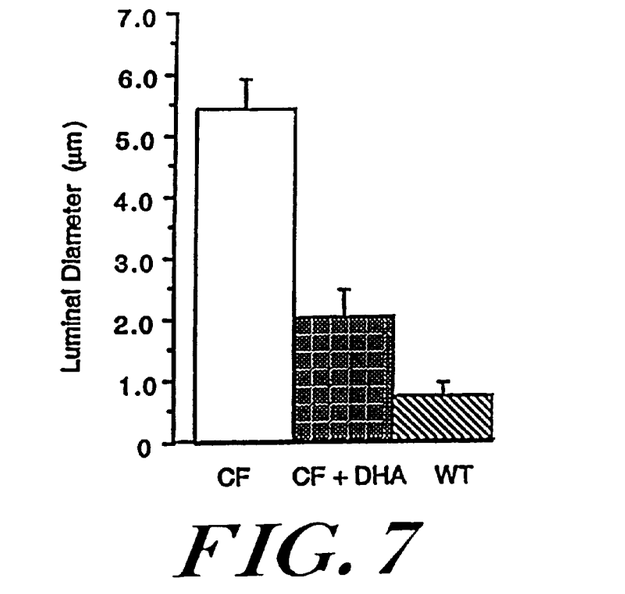
FIG. 7 is a bar graph depicting the pancreatic morphology from wild-type (WT), CFTR (−/−) mice (CF), and CFTR (−/−) mice treated orally with 40 mg per day of DHA for 7 days.

The results demonstrate that oral administration of DHA reverses pancreatic pathology in CFTR-/-mice fed with 40 mg of DHA per day for 7 days compared with CFTR-/-control mice. Tissue samples from these mice were prepared for light microscopy and sections analyzed at 200×. Pancreatic acinar cell morphology of CFTR-/-control mice is characterized by massive luminal dilatation and zymogen granule accumulation at the apical pole of the acinar cells (data not shown), two hallmark features of cystic fibrosis pathology (W.V.L. Go. (1993) Pancreas: Biology, Pathobiology, and Disease, Chapter 54:1041–1081). In sharp contrast, the wild-type and CFTR-/-mice fed with DHA both show no significant luminal dilatation, with zymogen granules more evenly dispersed within the cells. Iuminal diameter is approximately 9-fold greater in CFTR-/-mice. Oral DHA (40 mg/day) resulted in a 63% decrease in luminal diameter (p<0.0001, expressed as mean diameter ±S.D. (n=6)) (See FIG. 7). There also appeared to be a decrease in ductal plugs DGA-fed CFTR-/-mice; however, this observation was not subjected to morphometric analysis.

5. Oral administration of DHA reverses ileal pathology

Figure 8:
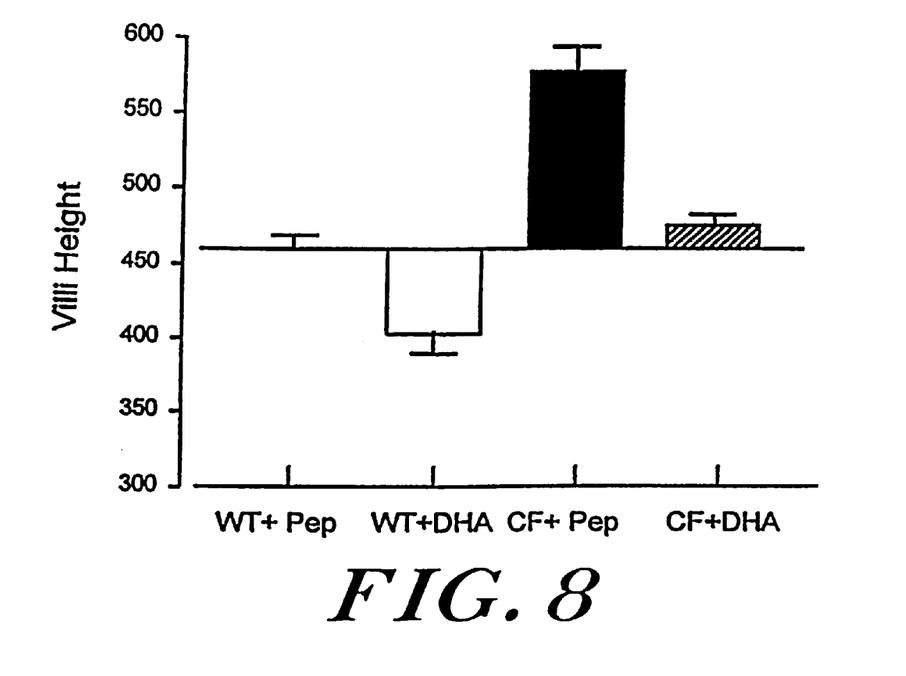
FIG. 8 is a bar graph depicting the ileal morphology from wild-type (WT), CFTR (−/−) (CF), and CFTR (−/−) mice treated orally with 40 mg per day of DHA for 7 days.

Although the lung displays minimal histologic changes in these CFTR-/-mice, ileal hypertrophy due to intestinal malabsorption is readily observed (Kent el al., (1996) Ped. Res. 40:233–241). Thus, the morphologic and morphometric studies utilized with the pancreas were also performed on the ileum. Tissue from the wild type and CFTR-/-mice was prepared for light microscopy and sections analyzed at 200×. Compared to wild-type mice, CFTR-/-mice demonstrate a dramatic increase in villus height (data not shown). Similar to results seen in the pancreas, oral DHA decreased villus height to that observed in wild-type mice. Morphometric analysis is shown in FIG. 8, the villous height was quantitated using NIH image software and expressed as mean diameter ±S.D. (n=6). This confirms that oral DHA restores villus height to normal wild-type values. These effects of DHA were only observed when CFTR-/-mice were fed 40 mg DHA per day and not with 10 mg or less.

Collectively, these results demonstrate that oral administration of high doses of DHA to CFTR-/-mice corrected the membrane lipid imbalance and reversed the pathological manifestations of cystic fibrosis. Formulations containing EPA and DHA have been given to cystic fibrosis patients in an effort to downregulate AA levels (Kurlandsky el al., (1994) *Pediatr. Pulmonol.* 18:24–27; Henderson et al., (1994) *J. Pediatr.* 124:400–408 and Sellmayer et al., (1996) *Lipids* 31:S37–S40). DHA absorption in these patients was comparable to that in control subjects and no toxic effects were observed. Although there may have been a slight clinical improvement in these patients, no statistically significant differences were found between control and cystic fibrosis patients. The DHA doses used in those studies was significantly lower than the equivalent doses (based on total calorie usage) used in the present invention to treat CFTR−/−mice. The plasma levels of DHA reported in those studies were 40–50 µg/ml corresponding to the levels obtained in our CFTR−/−mice using 0.5 mg DHA/day. The data demonstrates that administration of 0.5 mg/day of DHA to CFTR−/−mice does not significantly change phospholipid-bound AA and DHA levels nor has any significant effect on pancreas or ileal morphology. In addition, DHA formulations used in those clinical trials also contained EPA, known to compete with DHA for esterification at the sn-2 position of phospholipids.

Example 8

A. Administration of DHA and DHA precursors to wild-type and CFTR−/−Mice

In order to determine whether the observed decrease in DHA is the result of a block in the biosynthesis of DHA (22:6n-3) from α linolenic acid (18:3n-3) CFTR (−/−), mice were fed with 40 mg/day of either α linolenic acid or EPA (20:5n-3) for one week to magnify the accumulation of DHA precursors upstream from the putative block. Following weaning, wild-type and CFTR−/−mice were placed on water and Peptamen™ (a complete liquid enteral formulation comprised of medium-chain triglycerides, carbohydrates and hydrolyzed protein) ad lib until 30 days of age and then continued for 7 days with either Peptamen™, or with α-linolenic acid or EPA in a stable emulsion of Peptamen™ prepared by sonication. The volume of Peptamen™ administered was measured on a daily basis using specific feeders.

Administration of 40 mg/day of α-linolenic acid to CFTR−/−mice for one week resulted in a significant decrease in phospholipid-bound AA ($p<0.001$) and a further decrease in membrane-bound DHA ($p<0.001$). In addition, administration of α-linolenic acid resulted in increased intestinal villi height and a significant increase in acinar lumen dilatation and plug formation in the exocrine pancreas as compared to CFTR−/−controls treated with Peptamen™ (data not shown). In contrast, administration of 40 mg/day of α-linolenic acid to wild-type mice for one week resulted in an increase in membrane-bound DHA and a decrease in membrane-bound AA but did not produce and observable effects on pancreas morphology.

Eicosapentaenoic acid (EPA-20:5n-3), a DHA precursor downstream from α-linolenic acid, is known to effectively compete with AA for the site of esterification at the sn-2 position of membrane lipids. In order to ascertain whether the increase in AA observed in CFTR−/−mice is responsible for the pathological manifestations of cystic fibrosis, CFTR−/−mice were fed with 40 mg/day of EPA for one week to down-regulate membrane-bound AA levels. The results from these studies demonstrated that administration of EPA resulted in a significant increase in membrane-bound EPA, a significant decrease in membrane bound AA, and no significant changes in DHA/levels or pancreas morphology.

B. The effect of administration of DHA precursor 22:5n-3

Additional experiments were performed to observe the effect of administering the DHA precursor docosapentaenoic acid (DPA,22:5n-3) on DHA levels. Wild-type and CFTR−/−mice were fed with 40 mg of DPA per day for 7 days and fatty acids in pancreas and lung analyzed by GC/MS. One to 2 mm pieces of pancreas from both wild-type and CFTR−/−were fixed for 1.5 h in 25 glutaraldehyde in 0.2M cacodylate buffer and processed for morphometric analysis.

The results of these experiments are shown in Table 7. Administration of DPA to CFTR−/−mice resulted in an increase in membrane-bound DHA and DPA, and a decrease in membrane-bound AA in both pancreas and lung. In addition, DPA levels in pancreas and lung were significantly higher in CFTR−/−compared to wild-type mice suggesting the existence of a partial block in DHA biosynthesis downstream from DPA. Administration of 40 mg per day of DPA for 7 days to CFTR (−/−) mice resulted in a 20% improvement in pancreas morphology, as determined by measuring pancreatic ductal diameter and the presence of plugs.

TABLE 7

AA and DHA levels in wild-type and CFTR−/− mice fed with DPA-22:5n-3

| Fatty acid | Pancreas | Lung |
|---|---|---|
| Wild-type | | |
| 20:4n-6 | 6.8 ± 0.6 (13.3) | 7.8 ± 0.9 (17.5) |
| 20:5n-3 | 7.5 ± 0.8 (0.07) | 8.6 ± 0.8 (0.07) |
| 22:6n-3 | 2.5 ± 0.4 (1.5) | 7.5 ± 0.8 (4.0) |
| CFTR (−/−) | | |
| 20:4n-6 | 5.1 ± 0.6[1] (13.3) | 5.8 ± 0.9 (17.5) |
| 20:5n-3 | 14.6 ± 1.1 (0.1) | 15.6 ± 1.1 (0.1) |
| 22:6n-3 | 2.0 ± 0.4 (1.5) | 5.5 ± 0.8 (4.0 |

[1]values are expressed in nmoles of fatty acid per mg of protein and represent the mean of two experiments. Numbers in parenthesis correspond to values obtained in CFTR−/− control mice fed with Peptamen ™ alone.

Example 9

Effects of DHA administration to wild-type pregnant mice on fetal lung surfactant biosynthesis.

The invention also provides a method for improving the amount of fetal lung surfactant in a mouse model. It appears that this is accomplished by upregulating fetal lung surfactant biosynthesis during pregnancy. This method again utilizes giving high doses of DHA which increases DHA and fetal surfactant levels in the fetal lung. Gestation in mice lasts about 19.5 days and previous reports have shown that surfactant levels in amniotic fluid are not detected until after day 16.5, equivalent to about 30 to 32 weeks gestational age in humans. Wild-type C57 mice were bred and identification of the cervical plug was used to determine the occurrence of pregnancy and gestational age.

Beginning on day 9.5 of pregnancy (equivalent to about 24 weeks of gestational age in humans), mice were placed on Peptamen™ ±DHA for one week at different doses and sacrificed on day 16.5. Following sacrifice, amniotic fluid was aspirated from the amniotic sacs, and DPPC concentration determined by micro-HPTLC. In a different set of experiments, fetal lung and brain were removed, homogenized, lipids extracted with chloroform-methanol, and fatty acids transmethylated and analyzed by gas chromatography. The results showed that treatment of wild-type pregnant mice with an enteral formulation containing 20 mg per day of docosahexaenoic acid from day 9.5 to day 16.5 of gestation (equivalent to 24 weeks and 30 weeks gestational age in women, respectively), resulted in a DPPC concentration in amniotic fluid similar to that found on day 19.5 of gestation (equivalent to 38 weeks of gestational age in women), as measured by the DPPC test (Table 10). Newborns from treated and untreated pregnant mice were monitored for up to one month and no obvious long-term side effects of DHA were noted.

TABLE 8

DHA concentration in fetal lung

| Therapy | [DHA] |
|---|---|
| 16.5 day control | 13.1 ± 1.2[1] |
| 19.5 day control | 34.1 ± 4.6 |
| 16.5 + 20 mg/day DHA | 29.8 ± 5.5 |

[1]values are expressed in nmoles/mg protein and represent the mean ±SD of at least two experiments

TABLE 9

DHA concentration in fetal brain

| Therapy | [DHA] |
|---|---|
| 16.5 day control | 3.2 ± 0.4[1] |
| 19.5 day control | 4.7 ± 0.6 |
| 16.5 + 10 mg/day DHA | 15.6 ± 1.1 |
| 16.5 ± 20 mg/day DHA | 28.9 ± 1.9 |

[1]values are expressed in nmoles/mg protein and represent the mean ±SD of at least two experiments

TABLE 10

DPPC concentration in amniotic fluid from pregnant wild-type mice

| Therapy | [DPPC] |
|---|---|
| 16.5 day control | 6.6 ± 1.2[1] |
| 17.5 day control | 9.1 ± 2.5 |
| 19.5 day control | 14.7 ± 4.1 |
| 16.5 + 5 mg/day DHA | 9.3 ± 2.6 |
| 16.5 + 20 mg/day DHA | 18.0 ± 3.6 |

[1]values are expressed in $\mu$g/ml represent the mean ±SD of at least two experiments Collectively, the data shows that there was a significant increase in DHA content in both lung and brain as a function of gestational age and that DHA readily crosses the placenta in pregnant mice and is incorporated at significant levels in fetal lung and brain (see Tables 8 and 9). The data also demonstrates that DHA therapy increases surfactant concentration in preterm amniotic fluid to levels normally found at term (Table 10). Furthermore, these results are obtained with no observed side effects during the course of the studies.

Example 10

DHA and AA Levels in Blood Components Following DHA Therapy

In this Example, levels of DHA and AA in various blood components following administration of 40 mg DHA/day to mice was determined. In particular, 40 mg DHA was given to wild type mice and levels of DHA (Table 11) and AA (Table 12) were measured in plasma, red blood cells (RBC), and the pancreas. The results show that levels in the pancreas are paralleled in red blood cells and plasma. Accordingly, either plasma or red blood cell levels of DHA and AA (and their ratios) can be used as a diagnostic or to determine the effectiveness of treatment in the pancreas and other affected organs.

TABLE 11

Phospholipid-bound DHA levels in plasma, red blood cells, and pancreas in wild-type mice

| Day | Plasma | RBC | Pancreas |
|---|---|---|---|
| 0 | 45* | 0.62** | 61.5*** |
| 2 | 51 | 0.84 | 67.8 |
| 4 | 79 | 1.24 | 101.0 |
| 7 | 161 | 2.30 | 125 |

*values are expressed in $\mu$g/ml
**values are expressed in nmoles/100 million cells
***values are expressed in nmoles per total extract

TABLE 12

Phospholipid-bound AA levels in plasma, red blood cells, and pancreas in wild-type mice following administration of 40 mg DHA/day

| Day | Plasma | RBC | Pancreas |
|---|---|---|---|
| 0 | 256* | 12** | 293*** |
| 2 | 227 | 10.1 | 262 |
| 4 | 123 | 6.2 | 139 |
| 7 | 84 | 3.7 | 104 |

*values are expressed in $\mu$g/ml
**values are expressed in nmoles/100 million cells
***values are expressed in nmoles per total extract Example 11

Effects of Fish Oil on Phospholipid-Bound AA and DHA Levels and Histopathology in Pancreas From CFTR-/-Mice In order to determine whether the observed effects of DHA in reversing the pathological manifestations of cystic fibrosis in CFTR-/-mice are the result of downregulation of AA levels or alternatively requires a concomitant increase in DHA levels, CFTR-/-mice were fed 40 mg/day for one week of other n-3 fatty acids known to compete with AA and DHA biosynthesis and/or esterification into membrane phospholipids. AA and DHA levels and pancreas morphology were determined and compared to Peptamen™ alone, shown in Table 13. Administration of α-linolenic acid (LNA), a fatty acid known to compete with AA and DHA for the same elongation and desaturation enzymes, resulted in a four-fold decrease in AA, a two-fold decrease in DHA, and a significant increase in ductal dilatation in pancreas. Administration of EPA, a fatty acid known to compete with AA for esterification at the sn-2 position of phospholipids, resulted in a four-fold decrease in AA and no significant changes in DHA levels or pancreas morphology. Similar to EPA, administration of a dose of fish oil equivalent to 40 mg DHA, 60 mg EPA, and 15 mg LNA resulted in a three-fold decrease in AA levels and no significant changes in DHA or pancreas histopathology. Administration of docosapentaenoic acid (DPA), a DHA precursor downstream from EPA, resulted in a four-fold decrease in AA, a two fold increase in DHA, and a slight improvement in pancreas morphology. In contrast, administration of DHA at the same concentration resulted in a four-fold decrease in AA, a five-fold increase in DHA, and normalization of pancreas morphology. These results suggest that reversal of pancreatic morphology in CFTR-/-mice requires an increase in membrane bound DHA and that down-regulation of AA alone is not sufficient to correct the histopathological manifestations of cystic fibrosis in pancreas from CFTR-/-mice.

TABLE 13

AA and DHA Levels in Pancreas From CFTR-/- Mice Treated with LNA, EPA, DPA, DHA, and Fish Oil

| Fatty Acid | AA (nmoles/mg) | DHA (nmoles/mg) |
|---|---|---|
| Control | 21.6 ± 7.6 | 1.5 ± 0.5 |
| LNA | 5.5 ± 0.8 | 0.7 ± 0.07 |
| EPA | 5.1 ± 0.3 | 2.2 ± 0.4 |
| DPA | 5.1 ± 0.6 | 3.7 ± 0.4 |
| DHA | 4.9 ± 1.8 | 7.9 ± 1.5 |
| Fish Oil | 8.3 ± 0.4 | 2.3 ± 0.2 | values represent the mean ± S.D. of at least two experiments.

The foregoing examples are purely illustrative and are not intended to be the limitation of the invention. Those skilled in the art can determine other modifications on the diet used herein. Such modifications which are included within the following claims.

What is claimed is:

1. A method of treating a subject sufferings from cystic fibrosis comprising administering to said subject a composition containing a therapeutically effective amount of an omega 3 fatty acid having 22–24 carbon atoms and 5 or more double bonds and being substantially free of eicosapentanoic acid.

2. The method of claim 1, wherein the DHA levels are raised in the plasma to at least about 170 µg/ml.

3. The method of claim 2, wherein the DHA levels are raised in the plasma to at least about 200 µg/ml to about 500 µg/ml.

4. The method of claim 1, wherein said fatty acid is DHA.

5. The method of claim 4, wherein a therapeutically effective amount of DHA is about 0.3–5% of total caloric intake.

6. The method of claim 5, wherein a therapeutically effective amount of DHA is about 0.5–3% of total caloric intake.

7. The method of claim 5, wherein said therapeutically effective amount of DHA produces a pancreatic AA/DHA ratio of about 0.2–1.5.

8. The method of claim 5, wherein said therapeutically effective amount of DHA produces a lung AA/DHA ratio of about 0.1–1.6.

9. The method of claim 5, wherein said therapeutically effective amount of DHA produces a blood AA/DHA ratio of about 0.1–1.6.

10. The method of claim 1, wherein said fatty acid is selected from the group consisting of docosapentacnoic acid, tetracosapentaenoic acid and tetracosahexaenoic acid.

11. The method of claim 10, wherein a therapeutically effective amount of said fatty acid is about 0.3–5% of total caloric intake.

12. The method of claim 10, wherein a therapeutically effective amount of said fatty acid is about 0.5–3% of total caloric intake.

13. The method of claim 1, wherein said fatty acid is administered as a part of a structured lipid.

14. The method of claim 13, wherein said fatty acid is located at $R_2$ position of said structured lipid.

15. A method of ameliorating the effects of cystic fibrosis in a newborn comprising administering to said subject a composition containing a therapeutically effective amount of an omega 3 fatty acid having 22–24 carbon atoms and 5 or more double bonds and being substantially free of eicosapentanoic acid to a mother during pregnancy such that the affects of cystic fibrosis in the newborn are ameliorated.

16. The method of claim 15, wherein said fatty acid is DHA.

17. The method of claim 15, wherein said fatty acid is selected from the group consisting of docosapentaenoic acid, tetracosapentaenoic acid and tetracosahexaenoic acid.

18. A method of restoring a normal morphology of a cell or a tissue which exhibits a disease morphology associated with cystic fibrosis comprising contacting said cell or tissue with a composition containing a therapeutically effective amount of an omega 3 fatty acid having, 22–94 carbon atoms and 5 or more double bonds and being substantially free of eicosapentanoic acid such that the normal morphology of the cell or tissue is restored.

19. The method of claim 18, wherein said fatty acid is DHA.

20. The method of claim 18, wherein said fatty acid is selected from the group consisting of docosapentaenoic acid, tetracosapentaenoic acid and tetracosahexaenoic acid.

21. The method of claim 18, wherein said cell is a pancreatic acinar cell or a lung cell.

22. The method of claim 18, wherein said cell is a cell containing the cystic fibrosis gene product.

23. The method of claim 18, wherein said contacting occurs in vitro or in vivo.

24. The method of claim 18, wherein said cell is in a subject.

25. A method of treating a subject suffering from cystic fibrosis comprising administering to said subject a composition containing a therapeutically effective amount of DHA said composition being substantially free of eicosapentanoic acid.

26. A method of ameliorating the effects of cystic fibrosis in a newborn comprising administering to said subject a composition containing a therapeutically effective amount of DHA, said composition being substantially free of eicosapentanoic acid to a mother during pregnancy such that the affects of cystic fibrosis in the newborn are ameliorated.

27. A method of restoring a normal morphology of a cell or a tissue which exhibits a disease morphology associated with cystic fibrosis comprising contacting said cell or tissue with a composition containing a therapeutically effective amount of DHA, said composition being substantially free of eicosapentanoic acid such that the normal morphology of the cell or tissue is restored.

* * * * *